United States Patent
Sawai

(10) Patent No.: US 9,616,069 B2
(45) Date of Patent: Apr. 11, 2017

(54) AQUEOUS COMPOSITION

(71) Applicant: KOWA COMPANY, LTD., Nagoya-shi (JP)

(72) Inventor: Isamu Sawai, Fuji (JP)

(73) Assignee: KOWA COMPANY, LTD., Nagoya-shi (JP)

( * ) Notice: Subject to any disclaimer, the term of this patent is extended or adjusted under 35 U.S.C. 154(b) by 0 days.

(21) Appl. No.: 15/060,927

(22) Filed: Mar. 4, 2016

(65) Prior Publication Data
US 2016/0256470 A1    Sep. 8, 2016

(30) Foreign Application Priority Data

Mar. 6, 2015 (JP) ................................. 2015-044210

(51) Int. Cl.
| | | |
|---|---|---|
| *A61K 31/551* | (2006.01) | |
| *A61K 9/08* | (2006.01) | |
| *A61K 47/02* | (2006.01) | |
| *A61K 45/06* | (2006.01) | |
| *A61K 31/18* | (2006.01) | |
| *A61K 31/433* | (2006.01) | |
| *A61K 31/382* | (2006.01) | |
| *A61K 31/542* | (2006.01) | |
| *A61K 9/00* | (2006.01) | |

(52) U.S. Cl.
CPC .......... *A61K 31/551* (2013.01); *A61K 9/0048* (2013.01); *A61K 9/08* (2013.01); *A61K 31/18* (2013.01); *A61K 31/382* (2013.01); *A61K 31/433* (2013.01); *A61K 31/542* (2013.01); *A61K 45/06* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 8,193,193 B2 * | 6/2012 | Mizuno | A61K 31/542 514/218 |
| 2006/0142270 A1 | 6/2006 | Sugimoto et al. | |
| 2007/0088021 A1 | 4/2007 | Hidaka et al. | |
| 2009/0118299 A1 | 5/2009 | Mizuno et al. | |
| 2014/0378441 A1 | 12/2014 | Ishibashi et al. | |

FOREIGN PATENT DOCUMENTS

| | | |
|---|---|---|
| JP | 4212149 | 1/2009 |
| JP | 4972552 | 7/2012 |
| JP | 5557408 | 7/2014 |
| WO | WO 2006/068208 A1 | 6/2006 |
| WO | WO 2006/115244 A1 | 11/2006 |

OTHER PUBLICATIONS

Database CAPLUS in STN, Acc. No. 2013:279189, Inoue et al., JP 2013035802 A (Feb. 21, 2013) (abstract).*

* cited by examiner

*Primary Examiner* — Brian J Davis
(74) *Attorney, Agent, or Firm* — Oblon, McClelland, Maier & Neustadt, L.L.P.

(57) ABSTRACT

Provided is a technology for suppressing discoloration of a halo-isoquinoline derivative-containing aqueous composition during high-temperature storage. Provided is an aqueous composition containing a compound of formula (1):

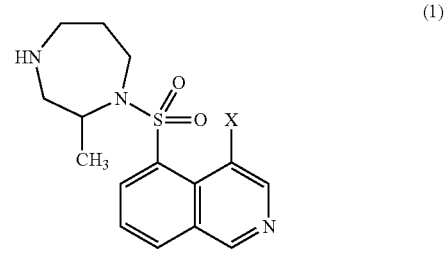

(1)

wherein X is a halogen atom, a salt of the compound, or a solvate of the compound or the salt; and a carbonic anhydrase inhibitor.

20 Claims, No Drawings

AQUEOUS COMPOSITION

CROSS REFERENCE TO RELATED APPLICATIONS

This application claims priority based on 35 U.S.C. 119 from prior Japanese Patent Application No. 2015-044210 filed Mar. 6, 2015, the contents of which are incorporated herein by reference in their entirety.

BACKGROUND

Technical Field

The present invention relates to an aqueous composition and the like.

Related Art

Halo-isoquinoline derivatives such as ripasudil (chemical name: 4-fluoro-5-{[(2S)-2-methyl-1,4-diazepan-1-yl]sulfonyl}isoquinoline) of the following formula:

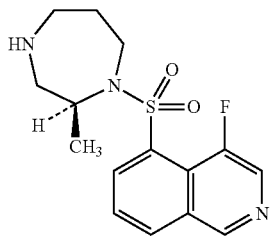 [SMILES: C[C@H]1CNCCCN1S(=O)(=O)c1cccc2cncc(F)c12]

and
4-bromo-5-{[(2S)-2-methyl-1,4-diazepan-1-yl]sulfonyl}isoquinoline of the following formula:

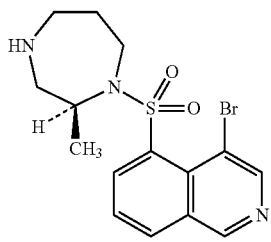 [SMILES: C[C@H]1CNCCCN1S(=O)(=O)c1cccc2cncc(Br)c12]

are known to have pharmacological activity such as Rho kinase-inhibitory activity (e.g., JP 4212149 B1 and WO 2006/115244 A) and to be useful for preventing or treating eye diseases. Specifically, for example, they are reported to be useful for preventing or treating ocular hypertension and glaucoma (e.g., WO 2006/068208 A) or for preventing or treating ocular fundus diseases such as age-related macular degeneration (e.g., JP 5557408 B1).

It is therefore very useful to establish a technology for stably formulating these halo-isoquinoline derivatives into, for example, preparations for ophthalmic application.

JP 4972552 B1 discloses that ripasudil ((S)-(−)-1-(4-fluoro-5-isoquinolinesulfonyl)-2-methyl-1,4-homopiperazine) or a salt thereof is administered in combination with brinzolamide, which is a carbonic anhydrase inhibitor. However, JP 4972552 B1 simply discloses that a solution containing 0.5% of ripasudil and an ophthalmic solution containing 1% of brinzolamide are sequentially dropped into the same eye of a rabbit. JP 4972552 B1 does not disclose at all an aqueous composition containing both of these compounds, storage of such an aqueous composition in a container, or storage stability of such an aqueous composition in a container over time.

SUMMARY OF THE INVENTION

Preparations for ophthalmic application are generally water-containing compositions (aqueous compositions). In order to formulate ripasudil (a halo-isoquinoline derivative) into a preparation for ophthalmic application, the inventor prepared an aqueous composition containing ripasudil and examined the storage stability of the aqueous composition. As a result, the inventor found that the aqueous composition has a problem that it suffers discoloration over time during storage at a high temperature.

It is therefore an object of the present invention to provide a technology for suppressing the discoloration of a halo-isoquinoline derivative-containing aqueous composition during high-temperature storage.

As a result of intensive studies to solve the problem, the inventor has accomplished the present invention on the basis of the findings that when a carbonic anhydrase inhibitor such as dorzolamide is added to an aqueous composition containing a halo-isoquinoline derivative such as ripasudil, the discoloration of the composition can be suppressed during high-temperature storage.

Specifically, according to the present invention, there is provided an aqueous composition containing:

a compound of formula (1):

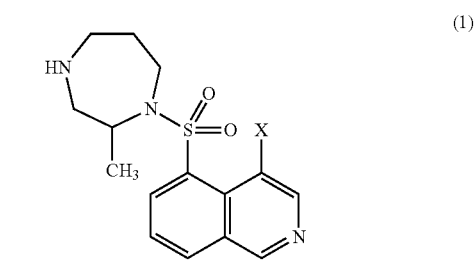

wherein X is a halogen atom, a salt of the compound, or a solvate of the compound or the salt; and a carbonic anhydrase inhibitor.

According to the present invention, there is provided a method for suppressing discoloration of an aqueous composition, the method including: the step of adding a carbonic anhydrase inhibitor to an aqueous composition containing a compound of formula (1) described above, a salt of the compound, or a solvate of the compound or the salt.

TECHNICAL EFFECT

The present invention makes it possible to suppress, during high-temperature storage, the discoloration of an aqueous composition containing a halo-isoquinoline derivative such as ripasudil.

DETAILED DESCRIPTION

The description discloses, for example, but not limited to, the following embodiments.

[1] An aqueous composition including:
a compound of formula (1):

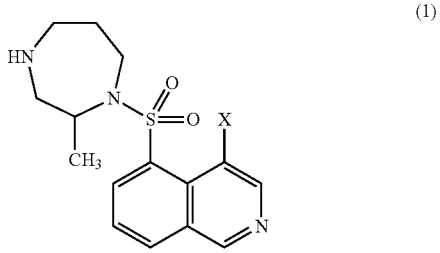

wherein X is a halogen atom,
a salt of the compound, or a solvate of the compound or the salt; and a carbonic anhydrase inhibitor.

[2] The aqueous composition according to [1], wherein the compound of formula (1) described above is ripasudil.

[3] The aqueous composition according to [1] or [2], wherein the carbonic anhydrase inhibitor is at least one selected from the group consisting of acetazolamide, dichlorphenamide, dorzolamide, brinzolamide, methazolamide, salts thereof, and solvates thereof.

[4] The aqueous composition according to [1] or [2], wherein the carbonic anhydrase inhibitor is at least one selected from the group consisting of dorzolamide, brinzolamide, salts thereof, and solvates thereof.

[5] The aqueous composition according to any one of [1] to [4], which is a preparation for ophthalmic application.

[6] The aqueous composition according to [5], which is an ophthalmic preparation.

[7] The aqueous composition according to any one of [1] to [6], which is an agent for preventing and/or treating a disease selected from the group consisting of ocular hypertension, glaucoma, and an ocular fundus disease.

[8] The aqueous composition according to any one of [1] to [7], further containing at least one selected from the group consisting of an α1 receptor blocker, an α2 receptor agonist, a β blocker, a prostaglandin, a sympathetic agent, a parasympathomimetic agent, a calcium antagonist, and a cholinesterase inhibitor.

[9] The aqueous composition according to any one of [1] to [7], further containing at least one selected from the group consisting of latanoprost, nipradilol, timolol, salts thereof, and solvates thereof.

[10] A pharmaceutical preparation containing: the aqueous composition according to any one of [1] to [9]; and a polyolefin resin container containing the aqueous composition.

[11] The pharmaceutical preparation according to [10], wherein the polyolefin resin is polyethylene or polypropylene.

[12] The pharmaceutical preparation according to [10] or [11], wherein the polyolefin resin container is an eye drop container.

[13] A method for suppressing discoloration of an aqueous composition, the method including: the step of adding a carbonic anhydrase inhibitor to an aqueous composition containing a compound of formula (1) described above, a salt of the compound, or a solvate of the compound or the salt.

[14] The method according to [13], wherein the compound of formula (1) is ripasudil.

[15] The method according to [13] or [14], wherein the carbonic anhydrase inhibitor is at least one selected from the group consisting of acetazolamide, dichlorphenamide, dorzolamide, brinzolamide, methazolamide, salts thereof, and solvates thereof.

[16] The method according to [13] or [14], wherein the carbonic anhydrase inhibitor is at least one selected from the group consisting of dorzolamide, brinzolamide, salts thereof, and solvates thereof.

[17] The method according to any one of [13] to [16], wherein the aqueous composition is a preparation for ophthalmic application.

[18] The method according to [17], wherein the preparation for ophthalmic application is an ophthalmic preparation.

[19] The method according to any one of [13] to [18], wherein the aqueous composition is an agent for preventing and/or treating a disease selected from the group consisting of ocular hypertension, glaucoma, and an ocular fundus disease.

[20] The method according to any one of [13] to [19], wherein the aqueous composition further contains at least one selected from the group consisting of an α1 receptor blocker, an α2 receptor agonist, a β blocker, a prostaglandin, a sympathetic agent, a parasympathomimetic agent, a calcium antagonist, and a cholinesterase inhibitor.

[21] The method according to any one of [13] to [19], wherein the aqueous composition further contains at least one selected from the group consisting of latanoprost, nipradilol, timolol, salts thereof, and solvates thereof.

[22] The method according to any one of [13] to [21], further including the step of adding the aqueous composition to a polyolefin resin container.

[23] The method according to [22], wherein the polyolefin resin is polyethylene or polypropylene.

[24] The method according to [22] or [23], wherein the polyolefin resin container is an eye drop container.

In formula (1) described above, the halogen atom may be, for example, a fluorine atom, a chlorine atom, or a bromine atom. In formula (1), the halogen atom is preferably a fluorine atom or a bromine atom, and more preferably a fluorine atom.

In formula (1) described above, the methyl-substituted carbon atom of the homopiperazine ring is an asymmetric carbon atom. Therefore stereoisomerism occurs. The compound of formula (1) is intended to include all possible stereoisomers. The compound of formula (1) may be a single stereoisomer or a mixture of different stereoisomers in any ratio. The compound of formula (1) preferably has the S absolute configuration.

The salt of the compound of formula (1) may be any pharmaceutically acceptable salt. Specifically, the salt may be, for example, an inorganic acid salt such as a hydrochloride, a sulfate, a nitrate, a hydrofluoride, or a hydrobromide; or an organic acid salt such as an acetate, a tartrate, a lactate, a citrate, a fumarate, a maleate, a succinate, a methanesulfonate, an ethanesulfonate, a benzenesulfonate, a toluenesulfonate, a naphthalenesulfonate, or a camphorsulfonate. A hydrochloride is preferred.

The compound of formula (1) or the salt thereof may form a solvate such as a hydrate or an alcohol solvate, and preferably forms a hydrate.

Specifically, the compound of formula (1), a salt thereof, or a solvate of the compound or the salt may be, for example, ripasudil (chemical name: 4-fluoro-5-{[(2S)-2-methyl-1,4-diazepan-1-yl]sulfonyl}isoquinoline), a salt thereof, or a solvate thereof; or 4-bromo-5-{[(2S)-2-methyl-1,4-diazepan-1-yl]sulfonyl}isoquinoline, a salt thereof, or a solvate thereof.

The compound of formula (1), a salt thereof, or a solvate of the compound or the salt is preferably ripasudil, a salt thereof, or a solvate of ripasudil or the salt, or 4-bromo-5-{[(2S)-2-methyl-1,4-diazepan-1-yl]sulfonyl}isoquinoline, a salt thereof, or a solvate thereof. The compound of formula (1), a salt thereof, or a solvate of the compound or the salt is more preferably ripasudil, a salt thereof, or a solvate of ripasudil or the salt, and even more preferably ripasudil, a hydrochloride thereof, or a solvate of ripasudil or the hydrochloride.

Ripasudil hydrochloride hydrate (ripasudil monohydrochloride dihydrate) of the following structural formula is particularly preferred.

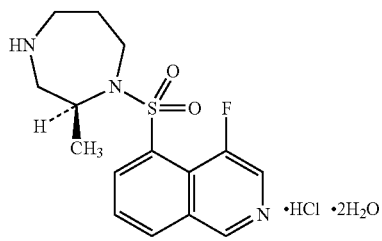 [SMILES: C[C@H]1CNCCCN1S(=O)(=O)c1cccc2cncc(F)c12 ; Cl ; "·2H2O"]

The compound of formula (1), a salt thereof, or a solvate of the compound or the salt is known in the art and can be produced by known methods. Specifically, ripasudil, a salt thereof, a solvate of ripasudil or the salt can be produced by, for example, the method described in WO 1999/020620 A or WO 2006/057397 A. Specifically, 4-bromo-5-{[(2S)-2-methyl-1,4-diazepan-1-yl]sulfonyl}isoquinoline, a salt thereof, or a solvate thereof can be produced by, for example, the method described in WO 2006/115244 A.

The content of the compound of formula (1), a salt thereof, or a solvate of the compound or the salt in the aqueous composition is not limited and may be appropriately determined taking into account the disease to be treated and the sex, age, condition, and other features of the patient. In order to obtain high pharmacological activity, the aqueous composition preferably contains from 0.01 to 10 w/v %, more preferably from 0.02 to 8 w/v %, and even more preferably from 0.04 to 6 w/v % (calculated in terms of the free form) of the compound of formula (1) in relation to the total volume of the aqueous composition. Particularly when ripasudil is used as the compound of formula (1), in order to obtain high pharmacological activity, the aqueous composition preferably contains from 0.05 to 5 w/v %, more preferably from 0.1 to 3 w/v %, and even more preferably from 0.15 to 2 w/v % (calculated in terms of the free form) of ripasudil, a salt thereof, or a solvate of ripasudil or the salt, in relation to the total volume of the aqueous composition.

In the description, the "carbonic anhydrase inhibitor" may be of any type having carbonic anhydrase inhibitory activity. Specifically, examples of the carbonic anhydrase inhibitor include, but are not limited to, acetazolamide, dichlorphenamide, dorzolamide, brinzolamide, methazolamide, pharmaceutically acceptable salts thereof, and solvates of these compounds or the pharmaceutically acceptable salts with water, an alcohol, or other solvents. These inhibitors may be used alone or in combination of two or more. Examples of the pharmaceutically acceptable salts include, but are not limited to, inorganic acid salts such as hydrochlorides, sulfates, nitrates, hydrofluorides, and hydrobromides; organic acid salts such as acetates, tartrates, lactates, citrates, fumarates, maleates, succinates, methanesulfonates, ethanesulfonates, benzenesulfonates, toluenesulfonates, naphthalenesulfonates, and camphorsulfonates; alkali metal salts such as sodium salts and potassium salts; and alkaline earth metal salts such as calcium salts and magnesium salts.

The carbonic anhydrase inhibitor is preferably at least one selected from the group consisting of acetazolamide, dichlorphenamide, dorzolamide, brinzolamide, methazolamide, salts thereof, and solvates thereof. The carbonic anhydrase inhibitor is more preferably at least one selected from the group consisting of acetazolamide sodium salt (chemical name: N-(5-sulfamoyl-1,3,4-thiadiazol-2-yl)-acetamide monosodium salt), dichlorphenamide (chemical name: 4,5-dichlorobenzene-1,3-disulfonamide), dorzolamide hydrochloride (chemical name: (4S,6S)-4-ethylamino-6-methyl-5,6-dihydro-4H-thieno[2,3-b]thiopyran-2-sulfonamide 7,7-dioxide monohydrochloride), brinzolamide (chemical name: (R)-4-(ethylamino)-3,4-dihydro-2-(3-methoxypropyl)-2H-thieno[3,2,e]-1,2-thiazine-6-sulfonamide 1,1-dioxide), and methazolamide (chemical name: 4-methyl-5-(acetylimino)-4,5-dihydro-1,3,4-thiadiazole-2-sulfonamide), even more preferably at least one selected from the group consisting of dorzolamide hydrochloride and brinzolamide, and further more preferably dorzolamide hydrochloride.

These carbonic anhydrase inhibitors are known in the art. These carbonic anhydrase inhibitors may be produced by known methods or may be commercially available products.

The content of the carbonic anhydrase inhibitor in the aqueous composition is not limited. In view of the discoloration-suppressing effect, the aqueous composition preferably contains from 0.01 to 5 w/v %, more preferably from 0.05 to 3 w/v %, and even more preferably from 0.1 to 2 w/v % of the carbonic anhydrase inhibitor, in relation to the total volume of the aqueous composition.

The aqueous composition may contain the compound of formula (1), a salt thereof, or a solvate of the compound or the salt and the carbonic anhydrase inhibitor in any weight ratio. In view of the discoloration-suppressing effect, the aqueous composition preferably contains from 0.05 to 15 parts by mass, more preferably from 0.25 to 7 parts by mass, and even more preferably from 0.75 to 4 parts by mass of the carbonic anhydrase inhibitor, in relation to 1 part by mass (calculated in terms of the free form) of the compound of formula (1). Particularly when the compound of formula (1), a salt thereof, or a solvate of the compound or the salt is ripasudil, a salt thereof, or a solvate of ripasudil or the salt, the aqueous composition preferably contains from 0.1 to 10 parts by mass, more preferably from 0.5 to 5 parts by mass, and even more preferably from 1 to 3 parts by mass of the carbonic anhydrase inhibitor, in relation to 1 part by mass (calculated in terms of the free form) of ripasudil, a salt thereof, or a solvate of ripasudil or the salt, in view of the discoloration-suppressing effect.

Particularly when the carbonic anhydrase inhibitor is dorzolamide, a salt thereof, or a solvate of dorzolamide or the salt, the aqueous composition preferably contains 0.01 to 5 w/v %, more preferably 0.05 to 3 w/v %, and even more preferably 0.1 to 2 w/v (calculated in terms of the free form) of dorzolamide, in relation to the total volume of the aqueous composition, in view of the discoloration-suppressing effect.

The aqueous composition may contain the compound of formula (1), a salt thereof, or a solvate of the compound or the salt and dorzolamide, a salt thereof, or a solvate of dorzolamide or the salt in any mass ratio. In view of the discoloration-suppressing effect, the aqueous composition preferably contains from 0.05 to 15 parts by mass, more preferably from 0.25 to 10 parts by mass, and even more preferably from 0.5 to 5 parts by mass (calculated in terms of the free form) of dorzolamide, a salt thereof, or a solvate of dorzolamide or the salt, in relation to 1 part by mass (calculated in terms of the free form) of the compound of formula (1). Particularly when the compound of formula (1), a salt thereof, or a solvate of the compound or the salt is ripasudil, a salt thereof, or a solvate of ripasudil or the salt, the aqueous composition preferably contains from 0.1 to 10 parts by mass, more preferably from 0.5 to 5 parts by mass, and even more preferably from 1 to 3 parts by mass (calculated in terms of the free form) of dorzolamide, a salt thereof, or a solvate of dorzolamide or the salt, in relation to 1 part by mass (calculated in terms of the free form) of ripasudil, a salt thereof, or a solvate of ripasudil or the salt, in view of the discoloration-suppressing effect.

When the carbonic anhydrase inhibitor is brinzolamide, a salt thereof, or a solvate of brinzolamide or the salt, the aqueous composition preferably contains from 0.02 to 10 w/v %, more preferably from 0.1 to 5 w/v %, and even more preferably from 0.2 to 3 w/v % (calculated in terms of the free form) of brinzolamide, in relation to the total volume of the aqueous composition, in view of the discoloration-suppressing effect.

The aqueous composition may contain the compound of formula (1), a salt thereof, or a solvate of the compound or the salt and brinzolamide, a salt thereof, or a solvate of brinzolamide or the salt in any mass ratio. In view of the discoloration-suppressing effect, the aqueous composition preferably contains from 0.1 to 20 parts by mass, more preferably from 0.5 to 15 parts by mass, and even more preferably from 1 to 10 parts by mass (calculated in terms of the free form) of brinzolamide, a salt thereof, or a solvate of brinzolamide or the salt, in relation to 1 part by mass (calculated in terms of the free form) of the compound of formula (1). Particularly when the compound of formula (1), a salt thereof, or a solvate of the compound or the salt is ripasudil, a salt thereof, or a solvate of ripasudil or the salt, the aqueous composition preferably contains from 0.2 to 10 parts by mass, more preferably from 1 to 10 parts by mass, and even more preferably from 1.5 to 5 parts by mass (calculated in terms of the free form) of brinzolamide, a salt thereof, or a solvate of brinzolamide or the salt, in relation to 1 part by mass (calculated in terms of the free form) of ripasudil, a salt thereof, or a solvate of ripasudil or the salt, in view of the discoloration-suppressing effect.

As used herein, the term "aqueous composition" means a composition containing at least water. The aqueous composition may be in a liquid state (a solution or a suspension) or a semi-solid state (an ointment) and is preferably in a liquid state. The water in the composition may be, for example, purified water, water for injection, or sterile purified water.

The content of water in the aqueous composition is preferably, but not limited to, 5% by mass or more, more preferably 20% by mass or more, even more preferably 50% by mass or more, further more preferably 90% by mass or more, and still more preferably from 90 to 99.8% by mass.

The aqueous composition may be formulated in various dosage forms by known methods described in, for example, The Japanese Pharmacopoeia, 16th Edition, General Rules for Preparations. Examples of dosage forms include injections, inhalants, ophthalmic preparations (ophthalmic liquids and solutions e.g., ophthalmic solutions, and ophthalmic suspensions), ophthalmic ointments, ear preparations, nasal solutions, enemas for rectal application, liquids and solutions for cutaneous application, sprays, ointments, gels, liquids and solutions for oral administration, and syrups. In order to take advantage of the pharmacological activity of the compound of formula (1), the dosage form of the aqueous composition is preferably a preparation for ophthalmic application, specifically, an ophthalmic preparation or an ophthalmic ointment, and more preferably an ophthalmic preparation.

Besides the ingredients described above, the aqueous composition may contain additives used in, for example, drugs or quasi drugs, depending on the dosage form. Example of such additives include inorganic salts, tonicity agents, chelating agents, stabilizers, pH regulators, antiseptics, antioxidants, thickening agents, surfactants, solubilizing agents, suspending agents, refreshing agents, dispersing agents, preservatives, oleagenous bases, emulsion bases, and water-soluble bases.

Specifically, examples of such additives include ascorbic acid, potassium aspartate, sodium hydrogen sulfite, alginic acid, sodium benzoate, benzyl benzoate, ε-aminocaproic acid, fennel oil, ethanol, ethylene-vinyl acetate copolymers, disodium edetate, tetrasodium edetate, potassium chloride, potassium chloride hydrate, sodium chloride, magnesium chloride, hydrochloric acid, alkyldiaminoethylglycine hydrochloride solution, carboxyvinyl polymers, dried sodium sulfite, dried sodium carbonate, d-camphor, dl-camphor, xylitol, citric acid hydrate, sodium citrate hydrate, glycerin, gluconic acid, L-glutamic acid, monosodium L-glutamate, creatinine, chlorhexidine gluconate solution, chlorobutanol, crystalline sodium dihydrogen phosphate, geraniol, sodium chondroitin sulfate, acetic acid, potassium acetate, sodium acetate hydrate, titanium oxide, gellan gum, dibutyl hydroxytoluene, potassium bromide, benzododecinium bromide, tartaric acid, sodium hydroxide, polyoxyl 45 stearate, purified lanolin, D-sorbitol, sorbitol solution, taurine, sodium hydrogen carbonate, disodium carbonate decahydrate, sodium thiosulfate hydrate, thimerosal, tyloxapol, sodium dehydroacetate, trometamol, concentrated glycerin, mixed tocopherol concentrate, white petrolatum, mentha water, mentha oil, benzalkonium chloride concentrated solution 50, ethyl parahydroxybenzoate, butyl parahydroxybenzoate, propyl parahydroxybenzoate, methyl parahydroxybenzoate, sodium hyaluronate, human serum albumin, hydroxyethylcellulose, hydroxypropylcellulose, hypromellose, glacial acetic acid, sodium pyrosulfite, phenylethyl alcohol, glucose, propylene glycol, bergamot oil, benzalkonium chloride, benzalkonium chloride solution, benzyl alcohol, benzethonium chloride, benzethonium chloride solution, borax, boric acid, povidone, polyoxyethylene (200) polyoxypropylene glycol (70), sodium polystyrene sulfonate, polysorbate 80, polyoxyethylene hydrogenated castor oil 60, partially hydrolyzed polyvinyl alcohol, d-borneol, Macrogol 4000, Macrogol 6000, D-mannitol, anhydrous citric acid, disodium hydrogen phosphate anhydrous, sodium dihydrogen phosphate anhydrous, methanesulfonic acid, methylcellulose, l-menthol, monoethanol amine, aluminum monostearate, polyethylene glycol monostearate, eucalyptus oil, potassium iodide, sulfuric acid, oxyquinoline sulfate, liquid paraffin, borneo camphor, phosphoric acid, dibasic sodium phosphate, monobasic potassium phosphate, sodium dihydrogen phosphate dihydrate, sodium dihydrogen phosphate monohydrate, malic acid, and petrolatum.

Preferred examples of the additives include potassium chloride, calcium chloride hydrate, sodium chloride, magnesium chloride, glycerin, acetic acid, potassium acetate, sodium acetate hydrate, tartaric acid, sodium hydroxide, sodium hydrogen carbonate, disodium carbonate decahydrate, concentrated glycerin, hydroxyethylcellulose, hydroxypropylcellulose, hypromellose, borax, boric acid, povidone, polysorbate 80, polyoxyethylene hydrogenated castor oil, polyethylene glycol monostearate, partially hydrolyzed polyvinyl alcohol, Macrogol 4000, Macrogol 6000, anhydrous citric acid, disodium hydrogen phosphate anhydrous, sodium dihydrogen phosphate anhydrous, methylcellulose, monoethanol amine, phosphoric acid, dibasic sodium phosphate, monobasic potassium phosphate, sodium dihydrogen phosphate dihydrate, sodium dihydrogen phosphate monohydrate, sodium hyaluronate, glucose, and l-menthol.

Besides the above ingredient, the aqueous composition may further contain an additional medicinal ingredient depending on the disease to be treated. Examples of such a medicinal ingredient include, but are not limited to, α1 receptor blockers including bunazosin, salts thereof (e.g., bunazosin hydrochloride), or solvates thereof; α2 receptor agonists including brimonidine, salts thereof (e.g., brimonidine tartrate), or solvates thereof, apraclonidine, salts thereof, or solvates thereof; β blockers including carteolol, salts thereof (e.g., carteolol hydrochloride), or solvates thereof, nipradilol, salts thereof, or solvates thereof, timolol, salts thereof (e.g., timolol maleate), or solvates thereof, betaxolol, salts thereof (e.g., betaxolol hydrochloride), or solvates thereof, levobunolol, salts thereof (e.g., levobunolol hydrochloride), or solvates thereof, befunolol, salts thereof, or solvates thereof, and metipranolol, salts thereof, or solvates thereof; prostaglandins including isopropyl unoprostone, salts thereof, or solvates thereof, tafluprost, salts thereof, or solvates thereof, travoprost, salts thereof, or solvates thereof, bimatoprost, salts thereof, or solvates thereof, and latanoprost, salts thereof, or solvates thereof: sympathetic agents including dipivefrine, salts thereof (e.g., dipivefrine hydrochloride), or solvates thereof, and epinephrine, salts thereof (e.g., epinephrine, epinephrine borate, and epinephrine hydrochloride), or solvates thereof; parasympathomimetic agents including distigmine bromide, salts thereof, or solvates thereof, pilocarpine, salts thereof (e.g., pilocarpine, pilocarpine hydrochloride, and, pilocarpine nitrate), or solvates thereof, and carbachol, salts thereof, or solvates thereof; calcium antagonists including lomerizine, salts thereof (e.g., lomerizine hydrochloride), or solvates thereof; and cholinesterase inhibitors including demecarium, salts thereof, or solvates thereof, echothiophate, salts thereof, or solvates thereof, and physostigmine, salts thereof, or solvates thereof. One or more of these agents may be added to the aqueous composition.

The additional medicinal ingredient is preferably at least one selected from the group consisting of latanoprost, nipradilol, timolol, salts thereof, and solvates thereof.

The pH of the aqueous composition is preferably, but not limited to, from 4 to 9, more preferably from 4.5 to 8, and even more preferably from 5 to 7. The osmotic pressure ratio of the aqueous composition to physiological saline is preferably from 0.6 to 3, and more preferably from 0.6 to 2.

In view of storage stability and portability, the aqueous composition is preferably stored in a container. As used herein, the term "container" means an enclosure capable of directly storing the aqueous composition. The container is intended to encompass all of "well-closed container," "tight container," and "hermetic container" defined in The Japanese Pharmacopoeia, 16th Edition, General Rules.

The container may be of any form capable of storing the aqueous composition. The form of the container may be appropriately selected and determined depending on the dosage form and other factors. Specifically, the form of the container may be, for example, an injection container, an inhalant container, a spray container, a bottle-shaped container, a tube-shaped container, an eye drop container, a nasal drop container, an ear drop container, or a bag container. These containers may further packed in a box, a bag, or any other package.

The material for the container (what the container is made of) is not particularly limited and may be appropriately selected depending on the form of the container. Specifically, the material may be, for example, glass, plastic, cellulose, pulp, rubber, or metal. In view of workability, squeezability, or durability, the container is preferably made of plastic. The plastic container is preferably made of a thermoplastic resin, examples of which include polyolefin resins such as low-density polyethylene (including linear low-density polyethylene), high-density polyethylene, medium-density polyethylene, polypropylene, and cyclic polyolefin; polyester resins such as polyethylene terephthalate, polybutylene terephthalate, polyethylene naphthalate, polybutylene naphthalate, and poly(1,4-cyclohexylenedimethylene terenaphthalate); polyphenylene ether resins; polycarbonate resins; polysulfone resins; polyamide resins; polyvinyl chloride resins; and styrene resins. The container may also be made of any blend (polymer alloy) thereof.

The material for the container is preferably, but not limited to, a polyolefin resin, and more preferably polypropylene, in view of the discoloration-suppressing effect. As shown in the test example below, discoloration is more effectively suppressed when the container is made of a polyolefin resin.

As used herein, the term "polyolefin resin container" means a container in which at least a part to be in contact with the aqueous composition is made of a "polyolefin resin." Therefore, for example, a container including an inner layer of polyolefin for coming into contact with the aqueous composition and an outer layer of another resin provided on the inner layer also corresponds to the "polyolefin resin container." In this regard, the polyolefin resin may be of any type, and may be a polymer of one monomer (homopolymer) or a copolymer of two or more monomers. Such a copolymer may be produced by any type of polymerization, and may be produced by random polymerization or block polymerization. The tacticity of the polyolefin resin is also not restricted.

Specifically, examples of the polyolefin resin as described above include polyethylene (more specifically, for example, low-density polyethylene (including linear low-density polyethylene), high-density polyethylene, or medium-density polyethylene), polypropylene, cyclic polyolefin, poly(4-methylpentene), polytetrafluoroethylene, ethylene-propylene copolymers, ethylene-α-olefin copolymers, ethylene-acrylic acid copolymers, ethylene-methacrylic acid copolymers, ethylene-vinyl acetate copolymers, and ethylene-ethyl acrylate copolymers. These resins may be used alone or in combination of two or more. In order to suppress discoloration, the polyolefin resin is preferably polyethylene, polypropylene, or cyclic polyolefin, more preferably polyethylene or polypropylene, and even more preferably polypropylene.

As used herein, the term "made of a polyolefin resin" means at least partially including a polyolefin resin as the material. For example, the term "made of a polyolefin resin" is intended to also include being made of a blend (polymer alloy) of two or more reins including a polyolefin resin and any other resin.

A material capable of blocking the transmission of ultraviolet light, such as an ultraviolet absorber or an ultraviolet scattering agent is preferably further added to the polyolefin resin container through kneading. This improves the stability of the compound of formula (1) against light. Examples of such an ultraviolet scattering agent include titanium oxide and zinc oxide. Examples of such an ultraviolet absorber include benzotriazole ultraviolet absorbers such as 2-(2H-benzotriazol-2-yl)-p-cresol (e.g., Tinuvin P (BASF)), 2-(2H-benzotriazol-2-yl)-4,6-bis(1-methyl-1-phenylethyl)phenol (e.g., Tinuvin 234 (BASF)), 2-(3,5-di-tert-butyl-2-hydroxyphenyl)benzotriazole (e.g., Tinuvin 320 (BASF)), 2-[5-chloro(2H)-benzotriazol-2-yl]-4-methyl-6-(tert-butyl)phenol (e.g., Tinuvin 326 (BASF)), 2-(3,5-di-tert-butyl-2-hydroxyphenyl)-5-chlorobenzotriazole (e.g., Tinuvin 327 (BASF)), 2-(2H-benzotriazol-2-yl)-4,6-di-tert-pentylphenol (e.g., Tinuvin PA328 (BASF)), 2-(2H-benzotriazol-2-yl)-4-(1,1,3,3-tetramethylbutyl)phenol (e.g., Tinuvin 329 (BASF)), 2,2'-methylenebis[6-(2H-benzotriazol-2-yl)-4-(1,1,3,3-tetramethylbutyl)phenol (e.g., Tinuvin 360 (BASF)), a reaction product of methyl 3-(3-(2H-benzotriazol-2-yl)-5-tert-butyl-4-hydroxyphenyl)propionate and polyethylene glycol 300 (e.g., Tinuvin 213 (BASF)), 2-(2H-benzotriazol-2-yl)-6-dodecyl-4-methylphenol (e.g., Tinuvin 571 (BASF)), 2-(2'-hydroxy-3',5'-di-tert-amylphenyl)benzotriazole, 2-[2'-hydroxy-3'-(3",4",5",6"-tetrahydrophthalimidomethyl)-5'-methylphenyl]benzotriazole, 2,2'-methylenebis[4-(1,1,3,3-tetramethylbutyl)-6-(2H-benzotriazol-2-yl)phenol; cyanoacrylate ultraviolet absorbers such as 2,2-bis{[2-cyano-3,3-diphenylacryloyloxy]methyl}propan-1,3-diyl=bis(2-cyano-3,3-diphenylacrylate) (e.g., Uvinul 3030 FF (BASF)), ethyl 2-cyano-3,3-diphenylacrylate (e.g, Uvinul 3035 (BASF)), and 2-ethylhexyl 2-cyano-3,3-diphenylacrylate (e.g., Uvinul 3039 (BASF)); triazine ultraviolet absorbers such as 2-(4,6-diphenyl-1,3,5-triazin-2-yl)-5-[(hexyl)oxy]-phenol (e.g., Tinuvin 1577 ED (BASF)); benzophenone ultraviolet absorbers such as octabenzone (e.g., Chimassorb 81 (BASF)), 2,2'-dihyroxy-4,4'-dimethoxybenzophenone (e.g., Uvinul 3049 (BASF)), 2,2'-4,4'-tetrahydrobenzophenone (e.g., Uvinul 3050 (BASF)), oxybenzone, hydroxymethoxybenzophenone sulfone, sodium hydroxymethoxybenzophenone sulfonate, dihydroxydimethoxybenzophenone, sodium dihydroxydimethoxybenzophenone disulfonate, dihydroxybenzophenone, and tetrahydroxybenzophenone; cinnamic acid ultraviolet absorbers such as diisopropyl methyl cinnamate, cinoxate, glyceryl di-p-methoxycinnamate mono-2-ethylhexanoate, a mixture of isopropyl p-methoxycinnamate and diisopropyl cinnamate, 2-ethylhexyl p-methoxycinnamate, and benzyl cinnamate; benzoate ultraviolet absorbers such as p-aminobenzoic acid, ethyl p-aminobenzoate, glyceryl p-aminobenzoate, amyl p-dimethylaminobenzoate, 2-ethylhexyl p-dimethylaminobenzoate, ethyl 4-[N,N-di(2-hydroxypropyl)amino]benzoate; salicylic acid ultraviolet absorbers such as ethylene glycol salicylate, octyl salicylate, dipropylene glycol salicylate, phenyl salicylate, homomentyl salicylate, methyl salicylate; guaiazulene; 2-ethylhexyl dimethoxybenzylidenedioxoimidazolidinepropionate; 2,4,6-tris[4-(2-ethylhexyloxycarbonyl)anilino]-1,3,5-triazine; p-hydroxyanisole; 4-tert-butyl-4'-methoxydibenzoylmethane; phenylbenzimidazole sulfonic acid; and hexyl 2-(4-diethylamino-2-hydroxybenzoyl)benzoate.

When a material capable of blocking the transmission of ultraviolet light is added to the container through kneading, the content of such a material in the container is, for example, generally from about 0.001 to about 50% by mass, preferably from about 0.002 to about 25% by mass, and more preferably from about 0.01 to about 10% by mass, while it depends on the type of the material and other factors.

The container is preferably such that its interior is visible (observable) to the naked eye. If its interior is visible, there will be some advantages such as the ability to check the presence or absence of contamination in the process of manufacturing pharmaceutical preparations and the ability of pharmaceutical preparation users to check the residual amount of the contents (aqueous composition). In this regard, the interior has only to be visible through at least part of the surface of the container (for example, the interior of an eye drop container can be made visible through its bottom surface even when a shrink film or the like is provided to make the interior invisible through its side surface). The aqueous composition in the container can be checked when its interior is visible through part of its surface.

The aqueous composition may be packed in the container by any means. The aqueous composition may be charged or added into the container by conventional methods depending on the form of the container and other conditions.

The disease to be treated with the aqueous composition or the pharmaceutical preparation is not restricted and may be appropriately selected depending on, for example, the pharmacological activity of the compound of formula (1).

The aqueous composition or the pharmaceutical preparation may be used as an agent for preventing or treating ocular hypertension or glaucoma on the basis of the Rho kinase-inhibiting activity or ocular tension-reducing effect of the compound of formula (1) or on the basis of the ocular tension-reducing effect of the carbonic anhydrase inhibitor. In this case, the ocular tension-reducing effect of the compound of formula (1) and the ocular tension-reducing effect of the carbonic anhydrase inhibitor can produce a higher level of ocular tension-reducing effect so that a higher level of ocular hypertension- or glaucoma-preventing and/or treating effect can be obtained, which is preferred. In this regard, more specific examples of glaucoma include primary open angle glaucoma, normal intraocular pressure glaucoma, hypersecretion glaucoma, acute angle-closure glaucoma, chronic angle-closure glaucoma, plateau iris syndrome, combined-mechanism glaucoma, steroid-induced glaucoma, capsular glaucoma of crystal lens, pigmentary glaucoma, amyloid glaucoma, neovascular glaucoma, and malignant glaucoma.

As disclosed in JP 5557408 B1, on the basis of the activity of the compound of formula (1), the aqueous composition or the pharmaceutical preparation may be used as an agent for preventing or treating ocular fundus diseases (lesions mainly of the retina and/or the choroid, specific examples of which include hypertensive or arteriosclerotic ocular fundus abnormalities, central retinal artery occlusion, retinal vein occlusion such as central retinal vein occlusion or branch retinal vein occlusion, diabetic retinopathy, diabetic macular edema, diabetic maculopathy, Eales disease, congenital retinal vascular abnormality such as Coats disease, von Hippel disease, pulseless disease, macular diseases (e.g. central serous chorioretinopathy, cystoid macular edema, age-related macular degeneration, macular hole, myopic macular degeneration, vitreoretinal interface maculopathy, drug-related maculopathy, and heredomacular degeneration), retinal detachment (e.g. rhegmatogenous, tractional, and exudative retinal detachment), retinitis pigmentosa, and retinopathy of prematurity). More preferably, the aqueous composition or the pharmaceutical preparation may be used as an agent for preventing or treating diabetic retinopathy, diabetic macular edema, or age-related macular degeneration.

The aqueous composition or the pharmaceutical preparation may be administered one to three times a day when used as an agent for preventing and/or treating an eye disease (preferably a disease selected from the group consisting of ocular hypertension, glaucoma, and ocular fundus disease, and more preferably a disease selected from the group consisting of ocular hypertension and glaucoma).

EXAMPLES

Next, the present invention will be more specifically described with reference to examples, which, however, are not intended to limit the present invention.

In the test example shown below, ripasudil monohydrochloride dihydrate can be produced by, for example, the method described in WO 2006/057397 A.

Test Example 1

Storage Test

The aqueous compositions of Example 1 and Comparative Example 1 each containing the ingredients in the amounts per 100 mL as shown in Table 1 were prepared by a conventional method and then added to polypropylene containers, respectively.

Each resulting aqueous composition was stored at 80° C. for a week. The degree of the color change (yellowing) before and after the storage of the aqueous composition was evaluated by determining the difference (ΔYI) between the color of the aqueous composition before the storage and that after the storage using a color-difference meter (Spectrophotometer CM-700d (Konica Minolta Sensing Co., Ltd.)).

Table 1 shows the results.

TABLE 1

|  | Example 1 | Comparative Example 1 |
| --- | --- | --- |
| Ripasudil monohydrochloride dehydrate | 0.9792 g (corresponding to 0.8 g of free form) | 0.9792 g (corresponding to 0.8 g of free form) |
| Dorzolamide hydrochloride | 1.112 g (corresponding to 1 g of free form) | — |
| Sodium dihydrogen phosphate anhydrous | 0.4 g | 0.4 g |
| Glycerin | 2.136 g | 2.136 g |
| Benzalkonium chloride concentrated solution 50 | 0.002 mL | 0.002 mL |
| Sodium hydroxide | q.s. (pH 6.0) | q.s. (pH 6.0) |
| Purified water | 100 mL in total | 100 mL in total |
| ΔY1 | 0.4 | 6.0 |

The results in Table 1 show that the ΔYI value is significantly lower when the ripasudil-containing aqueous composition further contains dorzolamide than when it does not contain dorzolamide. Therefore, it has been found that the discoloration caused by high-temperature storage is suppressed when dorzolamide is added to the ripasudil-containing aqueous composition.

The test results above have demonstrated that when further containing a carbonic anhydrase inhibitor typified by dorzolamide, an aqueous composition containing the compound of formula (1) typified by ripasudil, a salt thereof, or a solvate of the compound or the salt is more resistant to discoloration (yellowing) even after the storage at a high temperature, and has high storage stability.

Production Examples 1 to 27

Aqueous compositions containing the ingredients in the amounts ((g) per 100 mL of each aqueous composition) as shown in Tables 2 to 4 can be produced by conventional methods.

TABLE 2

|  | Production Example 1 | Production Example 2 | Production Example 3 | Production Example 4 | Production Example 5 | Production Example 6 | Production Example 7 | Production Example 8 | Production Example 9 |
| --- | --- | --- | --- | --- | --- | --- | --- | --- | --- |
| Ripasudil monohydrochloride dihydrate (calculated in terms of free form) | 0.2 | 0.2 | 0.2 | 0.4 | 0.4 | 0.4 | 0.8 | 0.8 | 0.8 |
| Dorzolamide hydrochloride (calculated in terms of free form) | 0.5 | 1 | 2 | — | — | 0.5 | 1 | 2 | — |
| Brinzolamide | — | — | — | 0.2 | 1 | — | — | — | 1 |
| Sodium chloride | 0.65 | — | — | — | 0.3 | 0.3 | 0.3 | 0.3 | — |
| Glycerin | — | 2 | — | — | 1 | — | — | 0.5 | 1 |
| Propylene glycol | — | — | 2 | — | — | 1 | — | 0.5 | 1 |
| Potassium chloride | — | — | — | 0.6 | — | — | 0.3 | — | — |
| Boric acid | — | — | — | — | — | — | — | — | — |
| Borax | — | — | — | — | — | — | — | — | — |
| Sodium dihydrogen phosphate monohydrate | 0.4 | 0.4 | 0.4 | — | — | 0.4 | 0.4 | 0.4 | 0.4 |
| Dibasic sodium phosphate | — | — | — | — | — | — | — | q.s. | q.s. |
| Disodium hydrogen phosphate anhydrous | — | — | — | — | — | q.s. | q.s. | — | — |
| Monobasic potassium phosphate | — | — | — | 0.4 | 0.4 | — | — | — | — |
| Sodium hydroxide | q.s. | q.s. | q.s. | q.s. | q.s. | — | — | — | — |
| Trometamol | — | — | — | — | — | — | — | — | — |
| Hydrochloric acid | — | — | — | — | — | — | q.s. | q.s. | q.s. |
| Citric acid hydrate | 0.1 | — | — | — | — | 0.1 | — | — | — |
| Sodium acetate hydrate | — | 0.1 | — | — | — | 0.1 | — | — | — |

TABLE 2-continued

|  | Production Example 1 | Production Example 2 | Production Example 3 | Production Example 4 | Production Example 5 | Production Example 6 | Production Example 7 | Production Example 8 | Production Example 9 |
|---|---|---|---|---|---|---|---|---|---|
| Disodium edetate | — | — | — | 0.1 | — | — | 0.1 | — | — |
| Benzalkonium chloride | 0.001 | 0.005 | — | 0.001 | 0.005 | 0.01 | 0.001 | 0.005 | — |
| Benzethonium chloride | — | — | — | — | — | — | — | — | 0.01 |
| Methyl parahydroxybenzoate | — | — | 0.01 | — | — | — | 0.01 | — | — |
| Propyl parahydroxybenzoate | — | — | 0.01 | — | — | — | 0.01 | — | — |
| Chlorobutanol | — | — | — | 0.2 | — | — | — | 0.2 | — |
| Polysorbate 80 | 0.3 | — | — | 0.3 | 0.3 | — | — | 0.3 | 0.3 |
| Polyoxyethylene castor oil 60 | — | 0.3 | — | 0.3 | — | 0.3 | — | 0.3 | 0.3 |
| Polyethylene glycol monostearate | — | — | 1.5 | 1.5 | — | — | 1.5 | — | 1.5 |
| Purified water | 100 mL in total | 100 mL in total | 100 mL in total | 100 mL in total | 100 ml in total | 100 mL in total | 100 mL in total | 100 mL in total | 100 mL in total |
| pH | 5 | 5 | 6 | 6 | 6.5 | 6.5 | 4.5 | 4.5 | 4 |

TABLE 3

|  | Production Example 10 | Production Example 11 | Production Example 12 | Production Example 13 | Production Example 14 | Production Example 15 | Production Example 16 | Production Example 17 | Production Example 18 |
|---|---|---|---|---|---|---|---|---|---|
| Ripasudil monohydrochloride dihydrate (calculated in terms of free form) | 0.2 | 0.2 | 0.2 | 0.4 | 0.4 | 0.4 | 0.8 | 0.8 | 0.8 |
| Dorzolamide hydrochloride (calculated in terms of free form) | 0.5 | 1 | 2 | — | — | 0.5 | 1 | 2 | — |
| Brinzolamide | — | — | — | 0.2 | 1 | — | — | — | 1 |
| Timolol maleate (calculated in terms of free form) | — | — | — | 0.25 | 0.5 | — | — | 0.25 | 0.5 |
| Sodium chloride | 0.65 | — | — | — | 0.3 | 0.3 | 0.3 | 0.3 | — |
| Glycerin | — | 2 | — | — | 1 | — | — | 0.5 | 1 |
| Propylene glycol | — | — | 2 | — | — | 1 | — | 0.5 | 1 |
| Potassium chloride | — | — | — | 0.6 | — | — | 0.3 | — | — |
| Boric acid | 1.0 | 1.0 | 1.0 | 1.0 | 1.0 | 1.0 | 1.0 | 1.0 | 1.0 |
| Borax | — | — | — | — | q.s. | q.s. | — | — | — |
| Sodium dihydrogen phosphate monohydrate | — | — | — | — | — | — | — | — | — |
| Dibasic sodium phosphate | — | — | — | — | — | — | — | — | — |
| Disodium hydrogen phosphate anhydrous | — | — | — | — | — | — | — | — | — |
| Monobasic potassium phosphate | — | — | — | — | — | — | — | — | — |
| Sodium hydroxide | q.s. | q.s. | q.s. | q.s. | — | — | — | — | — |
| Trometamol | — | — | — | — | — | — | — | — | — |
| Hydrochloric acid | — | — | — | — | — | — | q.s. | q.s. | q.s. |
| Citric acid hydrate | 0.1 | — | — | — | — | 0.1 | — | — | — |
| Sodium acetate hydrate | — | 0.1 | — | — | — | 0.1 | — | — | — |
| Disodium edetate | — | — | — | 0.1 | — | — | 0.1 | — | — |
| Benzalkonium chloride | 0.001 | 0.005 | — | 0.001 | 0.005 | 0.01 | 0.001 | 0.005 | — |
| Benzethonium chloride | — | — | — | — | — | — | — | — | 0.01 |
| Methyl parahydroxybenzoate | — | — | 0.01 | — | — | — | 0.01 | — | — |
| Propyl parahydroxybenzoate | — | — | 0.01 | — | — | — | 0.01 | — | — |
| Chlorobutanol | — | — | — | 0.2 | — | — | — | 0.2 | — |
| Polysorbate 80 | 0.3 | — | — | 0.3 | 0.3 | — | — | 0.3 | 0.3 |
| Polyoxyethylene castor oil 60 | — | 0.3 | — | 0.3 | — | 0.3 | — | 0.3 | 0.3 |
| Polyethylene glycol monostearate | — | — | 1.5 | 1.5 | — | — | 1.5 | — | 1.5 |

TABLE 3-continued

|  | Production Example 10 | Production Example 11 | Production Example 12 | Production Example 13 | Production Example 14 | Production Example 15 | Production Example 16 | Production Example 17 | Production Example 18 |
| --- | --- | --- | --- | --- | --- | --- | --- | --- | --- |
| Purified water | 100 mL in total | 100 mL in total | 100 mL in total | 100 mL in total | 100 mL in total | 100 mL in total | 100 mL in total | 100 mL in total | 100 mL in total |
| pH | 5 | 5 | 6 | 6 | 6.5 | 6.5 | 4.5 | 4.5 | 4 |

TABLE 4

|  | Production Example 19 | Production Example 20 | Production Example 21 | Production Example 22 | Production Example 23 | Production Example 24 | Production Example 25 | Production Example 26 | Production Example 27 |
| --- | --- | --- | --- | --- | --- | --- | --- | --- | --- |
| Ripasudil monohydrochloride dihydrate (calculated in terms of free form) | 0.2 | 0.2 | 0.2 | 0.4 | 0.4 | 0.4 | 0.8 | 0.8 | 0.8 |
| Dorzolamide hydrochloride (calculated in terms of free form) | 0.5 | 1 | 2 | — | — | 0.5 | 1 | 2 | — |
| Brinzolamide | — | — | — | 0.2 | 1 | — | — | — | 1 |
| Timolol maleate (calculated in terms of free form) | — | — | — | 0.25 | 0.5 | — | — | 0.25 | 0.5 |
| Sodium chloride | 0.65 | — | — | — | 0.3 | 0.3 | 0.3 | 0.3 | — |
| Glycerin | — | 2 | — | — | 1 | — | — | 0.5 | 1 |
| Propylene glycol | — | — | 2 | — | — | 1 | — | 0.5 | 1 |
| Potassium chloride | — | — | — | 0.6 | — | — | 0.3 | — | — |
| Boric acid | — | — | — | — | — | — | — | — | — |
| Borax | — | — | — | — | — | — | — | — | — |
| Sodium dihydrogen phosphate monohydrate | — | — | — | — | — | — | — | — | — |
| Dibasic sodium phosphate | — | — | — | — | — | — | — | — | — |
| Disodium hydrogen phosphate anhydrous | — | — | — | — | — | — | — | — | — |
| Monobasic potassium phosphate | — | — | — | — | — | — | — | — | — |
| Sodium hydroxide | — | — | — | — | — | — | — | — | — |
| Trometamol | 1.5 | 1.5 | 1.5 | 1.5 | 1.5 | 1.5 | 1.5 | 1.5 | 1.5 |
| Hydrochloric acid | q.s. | q.s. | q.s. | q.s. | q.s. | q.s. | q.s. | q.s. | q.s. |
| Citric acid hydrate | 0.1 | — | — | — | — | 0.1 | — | — | — |
| Sodium acetate hydrate | — | 0.1 | — | — | — | 0.1 | — | — | — |
| Disodium edetate | — | — | — | 0.1 | — | — | 0.1 | — | — |
| Benzalkonium chloride | 0.001 | 0.005 | — | 0.001 | 0.005 | 0.01 | 0.001 | 0.005 | — |
| Benzethonium chloride | — | — | — | — | — | — | — | — | 0.01 |
| Methyl parahydroxybenzoate | — | — | 0.01 | — | — | — | 0.01 | — | — |
| Propyl parahydroxybenzoate | — | — | 0.01 | — | — | — | 0.01 | — | — |
| Chlorobutanol | — | — | — | 0.2 | — | — | — | 0.2 | — |
| Polysorbate 80 | 0.3 | — | — | 0.3 | 0.3 | — | — | 0.3 | 0.3 |
| Polyoxyethylene castor oil 60 | — | 0.3 | — | 0.3 | — | 0.3 | — | 0.3 | 0.3 |
| Polyethylene glycol monostearate | — | — | 1.5 | 1.5 | — | — | 1.5 | — | 1.5 |
| Purified water | 100 mL in total | 100 mL in total | 100 mL in total | 100 mL in total | 100 mL in total | 100 mL in total | 100 mL in total | 100 mL in total | 100 mL in total |
| pH | 5 | 5 | 6 | 6 | 6.5 | 6.5 | 4.5 | 4.5 | 4 |

Production Examples 28 to 54

Aqueous compositions of Production Examples 28 to 54 can be produced by conventional methods using the same amount of 4-bromo-5-{[(2S)-2-methyl-1,4-diazepan-1-yl]sulfonyl}isoquinoline instead of ripasudil monohydrochloride dihydrate on production examples 1 to 27, respectively.

Production Examples 55 to 108

Pharmaceutical preparations of Production Examples 55 to 108 can be produced by adding the aqueous compositions of Production Examples 1 to 54 to eye drop containers made of polypropylene, according to conventional methods, respectively.

Production Examples 109 to 162

Pharmaceutical preparations of Production Examples 109 to 162 can be produced by adding the aqueous compositions of Production Examples 1 to 54 to eye drop containers made of polyethylene, according to conventional methods, respectively.

INDUSTRIAL APPLICABILITY

The present invention makes it possible to provide aqueous compositions and pharmaceutical preparations with high storage stability, which can be advantageously used in the pharmaceutical industry and other industries.

What is claimed is:

1. An aqueous composition, comprising:
from 0.01 to 5 w/v % of a carbonic anhydrase inhibitor; and
from 0.01 to 10 w/v % of a compound of formula (1), a salt of the compound, or a solvate of the compound or the salt:

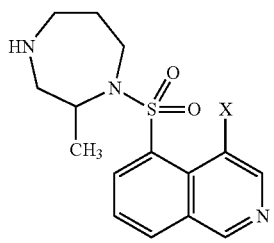

(1)

wherein X is a halogen atom.

2. The aqueous composition according to claim 1, wherein the compound of formula (1) is ripasudil.

3. The aqueous composition according to claim 1, wherein the carbonic anhydrase inhibitor comprises at least one of:
at least one compound (A) selected from the group consisting of acetazolamide, dichlorphenamide, dorzolamide, brinzolamide, and methazolamide;
a salt (B) of the compound (A);
a solvate of the compound (A); and
a solvate of the salt (B).

4. The aqueous composition according to claim 2, wherein the carbonic anhydrase inhibitor comprises at least one of:
at least one compound (A) selected from the group consisting of acetazolamide, dichlorphenamide, dorzolamide, brinzolamide, and methazolamide;
a salt (B) of the compound (A);
a solvate of the compound (A); and
a solvate of the salt (B).

5. A pharmaceutical preparation, comprising:
the aqueous composition according to claim 1; and
a polyolefin resin container containing the aqueous composition.

6. The pharmaceutical preparation according to claim 5, wherein the polyolefin resin container comprises polypropylene.

7. A pharmaceutical preparation, comprising:
the aqueous composition according to claim 2; and
a polyolefin resin container containing the aqueous composition.

8. The pharmaceutical preparation according to claim 7, wherein the polyolefin resin container comprises polypropylene.

9. A pharmaceutical preparation, comprising:
the aqueous composition according to claim 3; and
a polyolefin resin container containing the aqueous composition.

10. The pharmaceutical preparation according to claim 9, wherein the polyolefin resin container comprises polypropylene.

11. A pharmaceutical preparation, comprising:
the aqueous composition according to claim 4; and
a polyolefin resin container containing the aqueous composition.

12. The pharmaceutical preparation according to claim 11, wherein the polyorefin resin container comprises polypropylene.

13. A method for suppressing discoloration of an aqueous composition containing a compound of formula (1), a salt of the compound, or a solvate of the compound or the salt, comprising:
mixing a carbonic anhydrase inhibitor with an aqueous composition containing a compound of formula (1), a salt of the compound, or a solvate of the compound or the salt to obtain a mixture including from 0.01 to 5 w/v % of the carbonic anhydrase inhibitor and from 0.01 to 10 w/v % of the compound, a salt of the compound, or a solvate of the compound or the salt, with respect to a total volume of the mixture:

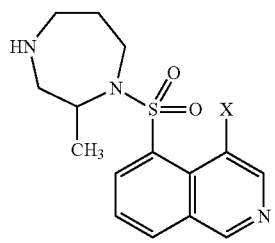

(1)

wherein X is a halogen atom, and suppressing discoloration is lowering a color difference ΔYI before and after storage of the mixture than a color difference ΔYI before and after the storage of a same mixture except for absence of the carbonic anhydrase inhibitor.

14. The method according to claim 13, wherein the compound of formula (1) is ripasudil.

15. The method according to claim 13, wherein the carbonic anhydrase inhibitor comprises at least one of:
at least one compound (A) selected from the group consisting of acetazolamide, dichlorphenamide, dorzolamide, brinzolamide, and methazolamide;
a salt (B) of the compound (A);
a solvate of the compound (A); and
a solvate of the salt (B).

16. The method according to claim 14, wherein the carbonic anhydrase inhibitor comprises at least one of:
at least one compound (A) selected from the group consisting of acetazolamide, dichlorphenamide, dorzolamide, brinzolamide, and methazolamide;
a salt (B) of the compound (A);
a solvate of the compound (A); and
a solvate of the salt (B).

17. The method according to claim 14, wherein the mixture includes from 0.05 to 5 w/v % of ripasudil with respect to the total volume of the mixture.

18. The method according to claim 14, wherein the mixture includes from 0.15 to 2 w/v % of ripasudil with respect to the total volume of the mixture.

19. The method according to claim 18, wherein the mixture includes brinzolamide in an amount of 0.2 to 3 w/v % with respect to the total volume of the mixture.

20. The method according to claim 13, wherein the storage is at 80° C. for a week.

* * * * *